United States Patent
Martens et al.

(10) Patent No.: US 6,875,899 B2
(45) Date of Patent: Apr. 5, 2005

(54) PRODUCTION OF HIGHER OLEFINS

(75) Inventors: Luc R.M. Martens, Meise (BE); John Stephen Godsmark, Grez Doicheau (BE); Marcel J. Janssen, Kessel-Lo (BE); Georges M. K. Mathys, Bierbeek (BE); Raphael F. Caers, Edegem (BE); Hubertus J. Beckers, Keerbergen (BE); J. Richard Shutt, Tervuren (BE); Eddy Van Driessche, Eeklo (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 514 days.

(21) Appl. No.: 10/056,839

(22) Filed: Jan. 24, 2002

(65) Prior Publication Data

US 2004/0133053 A1 Jul. 8, 2004

Related U.S. Application Data

(60) Provisional application No. 60/265,700, filed on Feb. 1, 2001.

(51) Int. Cl.[7] .............................................. C07C 1/207
(52) U.S. Cl. ....................... 585/327; 585/329; 585/634
(58) Field of Search ................................ 585/327, 324, 585/634

(56) References Cited

U.S. PATENT DOCUMENTS

| | | | |
|---|---|---|---|
| 3,407,789 A | 10/1968 | Hallee et al. | 122/356 |
| 3,647,682 A | 3/1972 | Rabo et al. | 208/120 |
| 3,820,955 A | 6/1974 | Woebcke | 23/227 R |
| 3,911,041 A | 10/1975 | Kaeding et al. | 260/682 |
| 4,499,055 A | 2/1985 | DiNicolantonio et al. | 422/197 |
| 4,814,067 A | 3/1989 | Gartside et al. | 208/127 |
| 4,828,679 A | 5/1989 | Cormier et al. | 208/120 |
| 4,861,939 A | 8/1989 | Debras et al. | 585/820 |
| 4,980,053 A | 12/1990 | Li et al. | 208/120 |
| 5,146,042 A | 9/1992 | Gurak et al. | 585/867 |
| 5,254,783 A | 10/1993 | Saleh et al. | 585/512 |
| 5,326,465 A | 7/1994 | Yongqing et al. | 208/120 |
| 5,432,243 A | 7/1995 | Bodart | 526/68 |
| 5,434,327 A | 7/1995 | Chin et al. | 585/533 |
| 5,672,800 A | 9/1997 | Mathys et al. | 585/520 |
| 5,714,662 A | 2/1998 | Vora et al. | 585/640 |
| 5,990,367 A | 11/1999 | Stine et al. | 585/514 |
| 6,049,017 A | 4/2000 | Vora et al. | 585/324 |
| 6,143,942 A | 11/2000 | Verrelst et al. | 585/533 |

FOREIGN PATENT DOCUMENTS

| | | | |
|---|---|---|---|
| EP | 1 127 862 | 8/2001 | C07C/2/18 |
| GB | 1343949 | 1/1974 | C07C/11/02 |

*Primary Examiner*—Thuan D. Dang

(57) ABSTRACT

A method of making a higher olefin product from a $C_4^+$ fraction separated from the hydrocarbon product produced by an oxygenate to olefin reaction unit. The $C_4^+$ fraction primarily contains butenes which may be directed to a higher olefin reaction unit without removing isobutenes, butanes, and/or butadiene. The $C_4^+$ fraction is particularly well suited for the production of higher olefins because of its high olefin content, low branching number, and low contaminent levels. The invention is also directed to an olefin product composition that is produced by contacting the $C_4^+$ fraction with an oligomerization catalyst. The olefin composition is characterized by a relatively high octene content, and octene with a branching number less than 1.4.

9 Claims, 2 Drawing Sheets

PRODUCTION OF HIGHER OLEFINS

This application claims priority to U.S. Provisional Patent Application No. 60/265,700, filed Feb. 1, 2001.

FIELD OF THE INVENTION

This invention relates to a system of making olefin derivatives, namely higher olefin, from olefin produced from an oxygenate. The higher olefin may then be used to produce a variety of olefin derivative products including alcohols, aldehydes, acids and esters.

BACKGROUND OF THE INVENTION

Olefins such as butenes and pentenes are useful in preparing a wide variety of derivative end products. Examples of such end products include alcohols, aldehydes acids and esters. The butenes and pentenes can also be oligomerized to form higher olefins having eight or more carbons. The higher olefins may be linear or they may have one or more alkyl branches. The higher olefins can then be converted to alcohols, aldehydes, acids and esters.

Butenes used in preparing olefin derivative products are typically made by cracking hydrocarbon feedstocks, i.e., producing low molecular weight hydrocarbons from high molecular weight hydrocarbons. Cracking of hydrocarbon feedstocks can be accomplished catalytically or non-catalytically. Non-catalytic cracking processes are described, for example, in Hallee et al., U.S. Pat. No. 3,407,789; Woebcke, U.S. Pat. No. 3,820,955; DiNicolantonio, U.S. Pat. No. 4,499,055 and Gartside et al., U.S. Pat. No. 4,814,067. Catalytic cracking processes are described, for example, in Cormier, Jr. et al., U.S. Pat. No. 4,828,679; Rabo et al., U.S. Pat. No. 3,647,682; Rosinski et al., U.S. Pat. No. 3,758,403; Gartside et al., U.S. Pat. No. 4,814,067; Li et al., U.S. Pat. No. 4,980,053; and Yongqing et al., U.S. Pat. No. 5,326,465.

One problem with using a hydrocarbon cracking unit to produce olefins is that the olefins contain a significant degree of alkyl branched olefin. For example, in a butenes stream, isobutene must first be removed before the butenes are directed to an oligomerization unit. The presence of isobutene in the butenes feed will result in branched higher olefin, which leads to branched alcohols. Branched alcohols have relatively little commercial value because they result in inferior plasticizers.

Another problem with olefin produced by a hydrocarbon cracking unit is that the olefin contains significant quantities of sulfur and nitrogen compounds. These compounds deactivate the acidic catalysts used in olefin derivative processes, such as olefin oligomerization. For example, Bodart, U.S. Pat. No. 5,432,243, and Debras et al., U.S. Pat. No. 4,861,939, disclose that arsine and carbonyl sulfide (COS) can be problematic in the olefin derivative process unless the contaminants are removed by additional purification equipment. U.S. Pat. No. 5,146,042 to Gurak et al. suggests that sulfur contaminants in $C_2$ to $C_4$ olefin can lead to undesirable side reactions in higher olefin and olefin derivative processes. Purification of such olefin requires that the contaminants be extracted into selected hydrocarbons followed by the distillation of the cleaned, lighter olefin from the hydrocarbons. Alternatively, nickel catalysts can be used to remove the sulfur contaminants. The equipment required to remove sulfur from an olefin is generally quite large in scale and quite expensive to operate.

Additional separations, such as diene removal, iso-alkene removal, and/or paraffin removal may be required depending upon the hydrocarbon source used in the cracking unit. As an example, the butenes stream from a hydrocarbon cracking unit contains significant amounts of butadiene and isobutene that must be removed. In U.S. Pat. No. 6,049,017 to Vora et al., the butadiene is removed by a controlled hydrogenation process. The isobutene is removed catalytically by contacting the butenes stream with methanol in a methyl-t-butylether (MTBE) reactor. The isobutene is converted to MTBE and the normal butenes and butane pass through the MTBE reactor. The normal butenes and butanes are then directed to a butane cracking unit to produce ethylene and propylene or to an oligomerization unit.

Generally, in the production of higher olefin, butanes are not removed from the butenes stream because a once through or low recycle higher olefin process is used. Instead, butanes are separated from the higher olefin product, which is a much easier and less costly separation. For example, the olefin content of a butenes stream from a steam cracking unit is typically about 60% by weight. The butenes stream is directed to the higher olefin unit at a conversion per pass of about 50% to 70%. There is little or no recycle, and the butanes are easily separated from the higher olefin product. However, there are several disadvantages to this process. One, 30% to 50% of the olefin in the feed is not converted to the desired product resulting in overall low process yields. Two, the high conversion per pass process results in a lower selectivity to the more desirable alpha-olefins. Alpha-olefins are olefins that contain the carbon-carbon double bond between the first and second carbon.

A high recycle, low conversion per pass process may address both of these disadvantages, however, such a process requires the availability of an olefin stream with a high olefin content to maintain the olefin concentration in the feed at an acceptable level. A butenes stream from a cracking unit, has a low olefin content. Consequently, a significant portion of the paraffins must be removed from the butenes stream if a high recycle, low conversion per pass process is to be used. This removal process can be a difficult and expensive task because of the relatively close boiling ranges of the components.

Removing various chemical contaminants from an olefin stream for producing an olefin derivative product can be a technically difficult process depending upon the feed specifications for the process. Therefore, if one could minimize or avoid the paraffin and contaminant removal process by having available an olefin stream with low levels of paraffin, alkyl branching, diene, and/or contaminant levels the costs of removing these components would be minimized or eliminated altogether.

SUMMARY OF THE INVENTION

The invention provides a method of making a higher olefin product, particularly a mixture of octenes, nonenes, and dodecenes from olefin produced from an oxygenate to olefin process. The method includes contacting an oxygenate with a molecular sieve catalyst to produce a hydrocarbon product containing olefin, separating a $C_4^+$ fraction containing four or more carbons from the hydrocarbon product, and contacting the $C_4^+$ fraction with an oligomerization catalyst to produce a product containing higher olefin. Optionally, a portion of the unreacted olefin that was not converted to product can be directed back to the $C_4^+$ fraction.

BRIEF DESCRIPTION OF THE DRAWINGS

This invention will be better understood by reference to the Detailed Description of the Invention when taken together with the attached drawings, wherein.

DETAILED DESCRIPTION OF THE INVENTION

Figure 1:
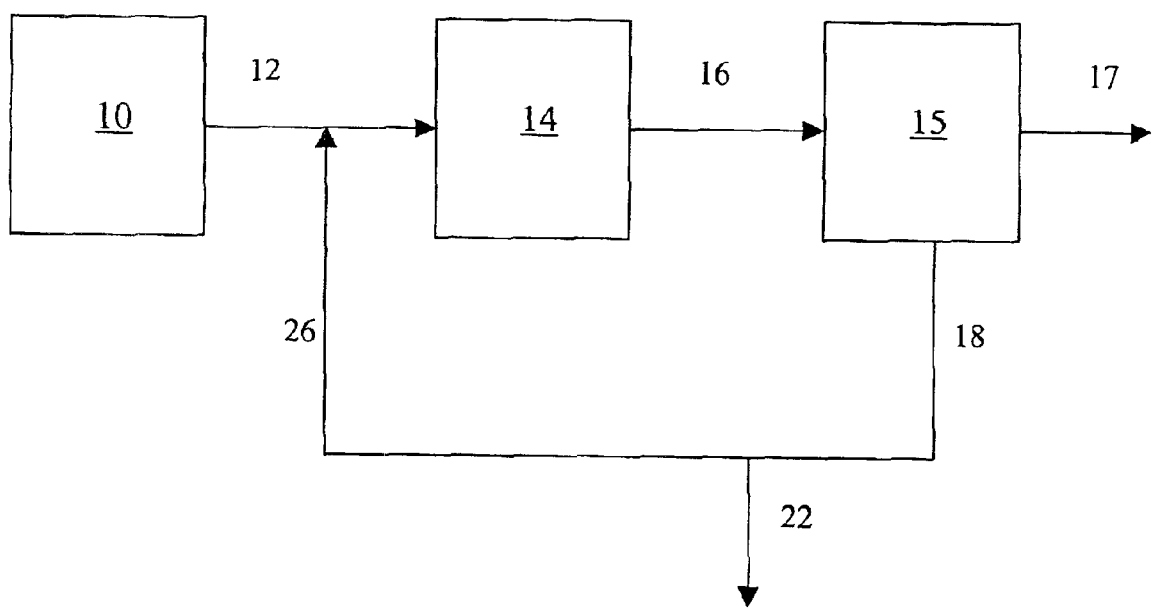
FIG. 1 is one embodiment for making a higher olefin.

In order to reduce the associated costs of producing higher olefins, this invention uses a portion of a hydrocarbon product from an oxygenate to olefin unit to make a novel hydrocarbon $C_4^+$ fraction. Preferably, the oxygenate to olefin unit is a methanol-to-olefin (MTO) unit. This $C_4^+$ fraction contains greater than 60% by weight, preferably greater than 80% by weight, $C_4^+$ olefin. The $C_4^+$ fraction contains a relatively high olefin content, i.e., low amounts of paraffin, very little diene, and relatively low degree of branched olefin. In the invention an olefin stream with greater than or equal to about 60% by weight olefin is referred to as an olefin stream having a high olefin content. Conversely, an olefin stream with less than about 60% by weight olefin is referred to an olefin stream having a low olefin content. Also, the $C_4^+$ fraction contains relatively little or no sulphur and nitrogen compounds that tend to deactivate oligomerization catalysts used in a higher olefin process.

This invention provides a higher olefin product containing significant amounts of octenes, nonenes, and dodecenes. The higher olefin can then be used to make higher alcohols, which may be used as a chemical feedstock for a number of commercial plasticizers. The process offers the advantage in that relatively expensive olefin purification equipment need not be used, or if used, smaller purification units are needed when the desired $C_4^+$ fraction is used. In large commercial scale processes, this results in a significant reduction in equipment costs as well as a significant reduction in operation costs. This reduction in equipment and operation costs ultimately provides the consumer with a product of the same high quality, but at significantly less cost.

In this invention, a hydrocarbon product from an oxygen to olefin reaction unit is directed to separation units, known in the art, to separate hydrocarbons according to carbon numbers. For example, methane is separated from the hydrocarbon product followed by, ethylene and ethane ($C_2$ separation), then propylene and propane ($C_3$ separation). The remaining portion of the hydrocarbon product, namely the portion containing predominantly four and five carbons ($C_4^+$ fraction), is directed to a higher olefin unit. Alternatively, the $C_4^+$ fraction can be separated in the beginning of the separation sequence to reduce the capacity requirements of the $C_2/C_3$ separation unit by as much as 10% to 25%.

The $C_4^+$ fraction contains greater than 60% by weight, preferably greater than 80% by weight, more preferably greater than 90% by weight, hydrocarbon having four and five carbons. The $C_4^+$ fraction contains greater than 60% by weight, preferably greater than 80% by weight, olefin having four carbons ($C_4$ olefin). Examples of olefin contained in $C_4^+$ fraction are 1-butene, cis and trans 2-butene, isobutene, and the pentenes. The $C_4^+$ fraction preferably contains from 60% to 97% by weight, preferably 80% to 97% by weight, olefin. The remainder of the $C_4^+$ fraction contains paraffin and small amounts of butadiene and other components. It is desirable that the $C_4^+$ fraction will more preferably have a compositional range as follows: 70% to 95% by weight, more preferably 80% to 95% by weight, normal butenes, which includes 1-butene and cis and trans 2-butene; 2 to 8% by weight, preferably less than 6% by weight, isobutene; 0.2% to 5% by weight, preferably less than 3% by weight butanes; 2% to 10% by weight, preferably less than 6% by weight, pentenes; and 2% to 10% by weight, preferably less than 5% by weight, propane and propylene.

It is also desired that the olefin $C_4^+$ fraction have a low branching number. It is desirable that the average branching number be less than 2.0, preferably less than 1.6, more preferably less than 1.4. The Average Branching Number (ABN) is defined as:

$$ABN = 1 + (1*\% \text{ monobranch} + 2*\% \text{ dibranched})/\% \text{ total olefin}$$

For example, if a dilute olefin stream has 20% 1-butene, 50% 2-butene, 10% butane, 10% isobutene, 5% propane, and 5% 3-methylbutene, the average branching number is about 1.17. An olefin having near 0% branched olefin will have a ABN of about 1.0.

In one embodiment, the $C_4^+$ fraction can be used as is, that is, directly from the separation unit to the higher olefin unit. Alternatively, there can be some further processing of the $C_4^+$ fraction before directing it to the higher olefin unit if desired. This may include a hydrogenation process that would selectively hydrogenate most if not all of the butadiene to butenes and a portion of the isobutene to isobutane. It is also important to limit the amount of isobutene in the olefin feed to minimize the amount of branched higher olefin product. Preferably, the $C_4^+$ fraction is directed to the higher olefin unit without butadiene or isobutene removal.

In another embodiment, purification of the $C_4^+$ fraction may require removal of low level impurities which will interfere with higher olefin reaction unit performance, and/or oxo (hydroformylation) catalyst performance. Low level contaminants will generally comprise polar molecules. Examples include oxygenates such as water, ethers, alcohols, and carboxylic acids. These compounds can be removed with various materials, such as solid molecular sieves, extraction with various solvents, and fractional distillation.

The $C_4^+$ fraction is typically low in contaminants such as hydrogen sulfide, carbonyl sulfide, and arsine. As a result, the $C_4^+$ fraction can be directed to a higher olefin unit with minimal separation and purification. In fact, following separation of the $C_4^+$ fraction from the oxygenate to olefin hydrocarbon product, removal of hydrogen sulfide, carbonyl sulfide, or arsine is often not necessary. Desirably, $C_4^+$ fraction will have a hydrogen sulfide content of less than 20 parts per million by weight (ppmw), preferably less than 5 ppmw., more preferably less than 1 ppmw. It is also desirable that $C_4^+$ fraction have a carbonyl sulfide content of less than 20 ppmw, preferably less than 5 ppmw., more preferably less than 1 ppmw. Likewise, it is desirably that $C_4^+$ fraction have an arsine content of less than 20 ppmw, preferably less than 5 ppmw, more preferably less than 1 ppmw.

Should additional purification of the olefin product stream be needed, purification systems such as that found in *Kirk-Othmer Encyclopedia of Chemical Technology*, 4th edition, Volume 9, John Wiley & Sons, 1996, pg. 894–899, the description of which is incorporated herein by reference, can be used. In addition, purification systems such as that found in *Kirk-Othmer Encyclopedia of Chemical Technology*, 4th edition, Volume 20, John Wiley & Sons, 1996, pg. 249–271, the description of which is also incorporated herein by reference, can be also be used.

In another embodiment, the $C_4^+$ fraction is directed to the higher olefin unit without separating hydrocarbons of different carbon number, olefin from paraffin of like carbon number, or directing the $C_4^+$ fraction to an MTBE unit to remove the isobutene or to a hydrogenation unit to remove butadiene and/or isobutene. As a result, dedicated facilities such as distillation units for separating $C_4$ from $C_5$ hydrocarbons or the butenes from butane, an MTBE unit, and a hydrogenation unit are not required prior to directing the $C_4^+$ fraction to the higher olefin unit.

In another embodiment, a portion of $C_4^+$ fraction that is not converted to product in the higher olefin unit is directed back to the $C_4^+$ fraction. As a result, the hydrocarbon feed to the higher olefin unit will have a different compositional make-up than the $C_4^+$ fraction. The hydrocarbon feed to the higher olefin unit will include hydrocarbons from a recycle stream, which will typically contain relatively more paraffin than the $C_4^+$ fraction. The compositional range of the hydrocarbon feed to the higher olefin unit depends upon the desired specifications of the higher olefin product, the oligomerization catalyst, the reaction conditions in the oligomerization unit, the amount of recycled hydrocarbon, and the composition of the $C_4^+$ fraction.

The low paraffin and contaminant content of $C_4^+$ fraction provides the operational flexibility of running a high recycle, low conversion per pass higher olefin process. The invention allows unreacted olefin from the higher olefin unit to be recycled without significantly adding to the overall load of the higher olefin unit and recovery facilities and without significant risk of accumulating contaminants that may deactivate the olgomerization catalyst. By using a feed that is low in paraffin and low in harmful contaminants with a higher olefin unit that utilizes a high recycle, low conversion per pass process, the overall yield and isomer selectivity of the higher olefin product can be significantly increased. A high recycle, low conversion per pass higher olefin process can convert greater than 80%, often greater than 90%, of the olefin in the process. Also, the high recycle provides greater operational flexibility to optimize the product selectivity to alpha-olefins, such as 1-octene.

In contrast, a conventional once through, high conversion higher olefin process will typically convert less than 80%, often less than 70%, of the olefin in the process. Also, because the conventional higher olefin unit operates at a relatively high conversion per pass, the selectivity to a more desirable higher olefin product is lower. Desired higher olefin product will contain relatively higher amounts of alpha-olefin and have a relatively low branching number.

A high recycle, low conversion per pass higher olefin process requires the availability of an olefin feed with a high olefin content to keep the purge volume to a minimum. In one embodiment, a $C_4^+$ fraction with a butenes concentration between 70 and 97% by weight is directed to a higher olefin unit. The $C_4^+$ fraction is mixed with the hydrocarbons from the recycle stream to produce an optimal hydrocarbon feed composition to the higher olefin unit. The optimal hydrocarbon feed composition will vary depending upon the recycle and olefin conversion percentages in the higher olefin unit. The hydrocarbon feed composition may vary between 20 to 95% by weight butenes. The paraffins are used as a diluent to control the rate of reaction in the higher olefin process. The low amount of paraffins in the $C_4^+$ fraction also minimizes the volume of purge gas needed to control the level of inerts in the hydrocarbon feed. This minimizes the amount of olefin lost in the purge stream.

The high recycle process will have an olefin conversion per pass ratio of between 30% and 70%, preferably between 40% and 70%, more preferably between 45% and 70%. The total olefin conversion can be as high as 80% to 98%, preferably from 90% to 98%. Another advantage of using a high recycle, low conversion per pass process is that the product selectivity, e.g., the isomer selectivity to 1-octene, can be optimized.

One embodiment of a high recycle process is shown in FIG. 1. $C_4^+$ fraction 12 produced in an oxygenate to olefin unit 10 is directed to a higher olefin unit 14. The product 16 containing higher olefin and unreacted olefin and paraffins is directed to a product separation unit 15. The higher olefin product 17, namely the octenes, nonenes and dodecenes, are separated from the unreacted olefin and paraffin, and then directed to additional separation units. These separation units are represented as 15b, 15c, 15d, and 15e in FIG. 2. The vent stream 18 contains unreacted olefin and inerts, including paraffins. The vent stream 18 comprises 40% to 90% by weight olefin. A portion of the vent stream 18 is removed via purge stream 22 to maintain the inerts balance in the higher olefin unit to a specific compositional range, which in turn maintains the olefins at the desired concentration in the hydrocarbon feed to the higher olefin unit 14. The remainder of the vent stream 18 is recycled to the olefin reaction unit 14 via recycle stream 26.

Another embodiment includes removing at least a portion of the paraffin and undesirable olefin from the vent stream 18 using one or more separation units. Examples of olefin separation units include fractional distillation equipment, including dephlegmators, and absorption, extractive or membrane separation equipment, and combinations thereof. Preferably, the olefin separation units are one or more fractional distillation units. Preferably, the fractional distillation unit is operated without the use of a lean physical solvent. Example compounds removed from the vent stream 18 include butane and isobutane. After a desired portion of such compounds have been removed as a purge stream, the desired separated olefins can be recycled to the higher olefin unit 14 via recycle stream 26.

Once the total amount of paraffins and olefin to the higher olefin unit 14 is set, the mass flow of vent stream 18 is determined by the desired extent of removal of the paraffin and olefin through olefin purge stream 22, and the recycle ratio in the process. In a preferred embodiment, at least 50% by weight of the paraffins in vent stream 18 are removed through purge stream 22, more preferably at least 75% by weight, and most preferably at least 90% by weight. A greater percentage of paraffins will be removed if a separation unit is positioned in the vent stream 18. Preferably, purge stream 22 will comprise no more than 50% by weight, more preferably no more than 20% by weight, and most preferably no more than 5% by weight, olefin.

Preferably the olefin recycle stream 26 comprises at least 50% by weight of the olefin contained in the vent stream 18, more preferably at least 75% by weight, and most preferably at least 90% by weight. The balance of the recovered olefin stream 26 may comprise paraffins and other materials found in the vent stream 18.

Most if not all known processes known in the art can be used to oligomerize $C_4^+$ fraction to higher olefins having eight or more carbons. Solid phosphoric acid polymerization is the commonly used process for the oligomerization of butenes. In the process the butenes are fed to a multibed reactor containing solid phosphoric acid, which is made from a pelletized and calcined mixture of phosphoric acid on kieselguhr. Operating conditions are 175° C. to 225° C. and pressures of at least 20 atm. The higher olefin selectivity is relatively poor, and for this reason the process is often associated with petroleum refining to ensure economical use of the less value products. Also, the disposal of the catalyst in landfills presents environmental issues and related costs.

Dimersol® is a commercial process that produces a more linear olefin than the phosphoric acid process. The reaction is carried out at 50° C. to 80° C. and about 1600 kPa to 1800 kPa in the liquid phase using a homogeneous nickel-alkyl aluminum catalyst. Ammonia and water are injected into the product stream to neutralize the catalyst, and the hydrocarbon is then separated from the aqueous phase. The catalyst is then recovered and recycled back to the reactor.

In another embodiment, a modified ZSM-22 catalyst can be used as an oligomerization catalyst. U.S. Pat. No. 6,013,851 to Verrelst et al., the disclosure of which is incorporated herein by reference, describes a modified ZSM-22 olefin oligomerization molecular sieve catalyst wherein the molecular sieve contains a metal-silicon core and surface layer, with the surface layer having a higher silicon metal ratio than that of the core. The metal is selected from aluminum, gallium and iron. This catalyst reduces the amount of branched higher olefin produced in the process. Also, the presence of some paraffin in the olefin feed has no or little effect on the catalytic efficiency of the catalyst. As a result, the relatively small amounts of butane in $C_4^+$ fraction does not have to be separated from the feed. For example, a 1:1, preferably 2:1, ratio of butene:butane can be used. Small amounts of water are also shown to enhance the production of desired higher olefin.

Using the modified ZSM-22 catalyst in a high recycle, higer olefin process the product selectivity to octene is retained with a decrease in the amount of branching. For example, using $C_4^+$ fraction as feed, octene selectivity can exceed 80%. An octene selectivity greater than 90% can be achieved with a higher recycle ratio. The oligomerization may take place at a temperature in the range of from 160° C. to 300° C., preferably from 170° C. to 260° C., and most preferably from 180° C. to 260° C., at a pressure advantageously in the range of from 5 MPa to 10 MPa, preferably from 6 MPa to 8 MPa, and at an olefin hourly space velocity advantageously in the range 0.1 $hr^{-1}$ to 20 $hr^{-1}$, preferably from 0.5 $hr^{-1}$ to 10 $hr^{-1}$, and most preferably 0.75 $hr^{-1}$ to 3.5 $hr^{-1}$.

In another embodiment, the oligomerization of $C_4^+$ fraction olefin can be carried out in the presence of a nickel oxide (NiO) catalyst as described in U.S. Pat. No. 5,254,783 to Saleh et al., the disclosure of which is incorporated herein by reference. The catalyst contains amorphous NiO present as a disperse monolayer on the surfaces of a silica support. The support also contains minor amounts of an oxide of aluminum, gallium or indium such that the ratio of NiO to metal oxide present in the catalyst is within the range of from about 4:1 to about 100:1. The catalyst converts linear butenes to octene products having on average less than about 2.6, generally less than 2.0 to 2.4. methyl groups per molecule.

The NiO catalyst is particularly effective for the dimerization of butene to form a mixed polymerization product composed mainly of octenes. Preferably, the $C_4^+$ OTO will not contain more than 5% by weight of isobutene, because isobutene tends to form products with a high degree of branching. The desired isobutene concentrations can be achieved by selectivity hydrogenating $C_4^+$ OTO. The presence of paraffins in the olefin feed is not generally detrimental, but if the proportion rises above 80% by weight the process becomes uneconomical.

The oligomerization using a NiO catalyst is carried out in either the liquid or gas phase. Temperature conditions include a temperature from 150° C. to 275° C. and, in the gas phase, a liquid hourly weight feed rate of butene over the catalyst of from 0.4 $hr^{-1}$ to 1.8 $hr^{-1}$, preferably from 0.6 $hr^{-1}$ to 0.7 $hr^{-1}$. Where the oligomerization reaction is conducted in the liquid phase and the catalyst is mixed with the olefin, it is preferred that the ratio of olefin to catalyst be in the range of from 2:1 to 8:1, more preferably from 4:1 to 6:1. In cases where the oligomerization is conducted under pressure near, at or above the critical temperature of the olefin, it is often desirable to insure that the liquid phase is maintained by carrying out the reaction in the presence of an inert higher boiling hydrocarbon such as a normal paraffin or cycloparaffin.

In another embodiment, a ZSM-57 catalyst can be used as an oligomerization catalyst. ZSM-57 provides high product selectivity to octenes with a decrease in the amount of branching product and cracking of the olefin. Also, the ZSM-57 catalyst exhibits a relatively higher reactivity with pentenes that are also present in $C_4^+$ OTO. As a result, the yield of nonenes is increased in the process. In fact, additional pentenes can be added to $C_4^+$ OTO from an external source to boost the yields of nonene in the process. The oligomerization may take place at a temperature in the range of from 80° C. to 400° C., preferably from 120° C. to 300° C., and most preferably from 150° C. to 280° C., at a pressure advantageously in the range of from 2 MPa to 15 MPa, preferably from 5 MPa to 10 MPa, and at an olefin hourly space velocity advantageously in the range 0.1 $hr^{-1}$ to 30 $hr^{-1}$, preferably from 0.5 $hr^{-1}$ to 15 $hr^{-1}$, and most preferably 0.75 $hr^{-1}$ to 8 $hr^{-1}$.

Figure 2:
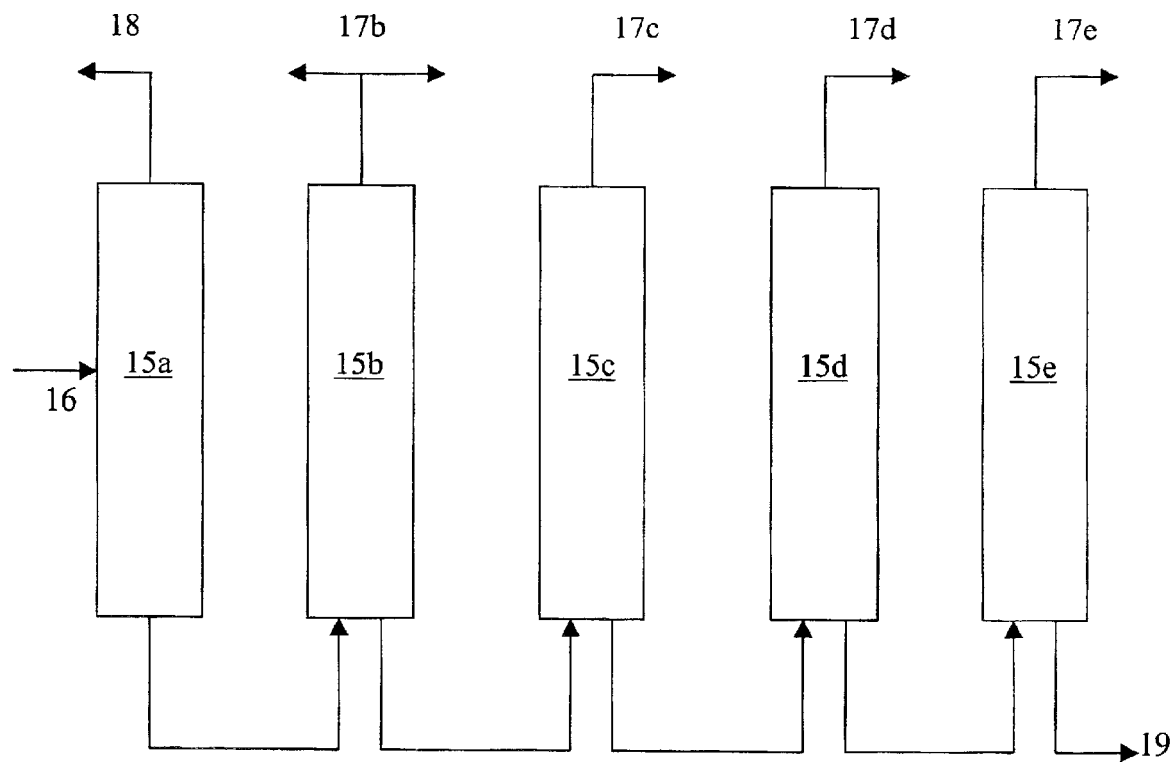
FIG. 2 is one embodiment for separating the higher olefin product into various olefinic components.

FIG. 2 depicts separation unit 15 divided into several separation units 15a, 15b, 15c, 15d, and 15e. In one embodiment, separation units 15a–15e can be designed as follows. Separation unit 15b removes the pentenes and hexenes 17b from the higher olefin product 16. The pentenes and hexenes 17b can be used as fuel and/or may also be directed to the higher olefin reaction unit 14. The recycled pentenes and hexenes 17b can combine with $C_4^+$ fraction 12 to form additional nonene and decane, respectively. Separation unit 15c removes the heptenes 17c, separation unit 15d removes the octenes 17d, and separation unit 15e removes the nonene 17e. Other separation units can be used to separate the remainder of the higher olefin product. For example, it may be desirable to separate the significant amount of dodecenes from the $C_{10}$–$C_{20}$ higher olefin 19 to produce $C_{13}$-alcohols. The $C_{10}$–$C_{20}$ higher olefin 19 can also be used as chemical feedstock for other commercial value products, such as jet fuel or high quality solvents. The separations according to carbon number may be carried out using methods known in the art as described in Kirk-Othmer, *Encyclopedia of Chemical Technology*, 4th edition, Volume 20, John Wiley & Sons, 1996, the disclosure of which is incorporated herein by reference.

Because $C_4^+$ OTO contains mostly butenes, the product expected from a higher olefin unit will contain primarily octenes (about 70%), dodecenes (about 17%) as well as some nonenes (about 5%) and $C_{16}$–$C_{20}$ alkenes (about 5%). These percentages will vary depending upon the type of oligomerization catalyst used and the hydrocarbon feed composition.

It may, be desirable to produce additional nonene from the higher olefin unit. One way of accomplishing this task is to feed additional $C_5$ olefin to the higher olefin unit. The source of the $C_5$ olefin may come from a steam cracker, or from the small amount produced by the higher olefin unit. Additional $C_5$ olefin may also be obtained from catalytically cracking the higher olefin product such as the heptane and $C_{10}$ to $C_{20}$ olefin.

Following separation of the higher olefin product into the desired higher olefin components based on carbon numbers, the respective separated higher olefin can be directed to one or more hydroformylation units. In one embodiment, the octenes and nonenes can be directed to hydroformylation units to produce nonanyl alcohol and decyl alcohol, respectively. The remaining portion of the higher olefin product, that is, higher olefin with ten or more carbons can be directed to a hydrogenation unit. The hydrogenated products can be used as blending components to increase the quality of diesel or aviation fuel. A portion of the octene and nonene not directed to the hydroformylation units may also be directed to the hydrogenation unit.

One hydroformulation process that may be used is commonly referred to as the oxo-process. In the oxo-process, an olefin reacts with carbon monoxide and hydrogen at elevated temperature and pressure in the presence of a catalyst to produce predominately two isomeric aldehydes: a terminal or normal, aldehyde, and an internal, or branched, aldehyde. The position of the formyl group in the aldehyde product depends upon the olefin, the catalyst, the solvent, and the reaction conditions. Typically, the use of catalysts with strictly encompassing complexing ligands, e.g., tertiary phosphines, results predominately in the formation of the normal aldehyde. In most commercial processes the initially formed aldehyde product is not isolated. Rather, the aldehydes are further converted to alcohols by a hydrogenation process or by an aldolization/hydrogeneration process. Purification of higher molecular weight alcohols usually includes low pressure distillation or separations involving falling film evaporators.

A variety of transition metals catalyze the conversion of olefin to aldehydes, but typically only cobalt and rhodium complexes are used in commercial oxo plants. A commercial oxo process involving a conventional cobalt catalyst may include at least the following steps: hydroformylation, that is, the formation of the aldehyde, removal and recovery of catalyst, aldehyde refining, hydrogenation, and finally alcohol refining. In addition, commercial plants may use the aldolization/hydrogenation process to convert the aldehydes to alcohols. Commercial hydroformylations are carried out continuously in either back mixed or tubular stainless steel reactors or in combinations of the two. In the back mixed reactor, the composition of the reaction mixture is constant and close to that of product. In the tubular reactor, the composition changes continually with time because of plug flow through long narrow tubes. Reaction conditions vary depending on the olefin feed, but generally are 100° C. to 180° C. and 20 MPa to 35 MPa. The pressure used is determined by the catalyst stability at a particular reaction temperature. Catalyst concentrations of about 0.1% to 1% cobalt based on olefin and liquid residence times of 1 hour to 2 hours are common.

Conversion of crude oxo aldehydes to alcohols is accomplished by heterogenous vapor or liquid phase hydrogenation in fixed bed reactors. Among the metals that have been used as catalysts for these hydrogenations are copper, nickel, tungsten, cobalt, molybdenum sulfide, and various combination of these metals. Because sulfur poisoning is not a concern in this invention, nickel or cobalt containing catalysts are preferred. Catalysts frequently are placed on inert supports by reaction of the corresponding metal oxides with hydrogen.

The hydrogenation of oxo-products are typically carried out at 100° C. to 250° C.; the specific conditions are dictated by the catalyst being used and the desired conversion. The vapor phase process is operated at low pressures, and the liquid phase process is operated up to pressures of 35 MPa. Internal or external cooling, or both, are required to remove heat from the reaction.

The use of a cobalt carbonyl catalyst modified by organic phosphine ligands can significantly improve hydroformylation selectivity to the more desirable terminal aldehydes, which in turn will most likely lead to terminal alcohols. Although these phosphine modified, cobalt catalysts are less reactive than uncomplexed cobalt carbonyls, they can be used at higher reaction temperatures, i.e., 150° C. to 210° C., and lower pressures 2 MPa to 10 MPa. These catalysts are also active hydrogeneration catalysts. As a result, the hydroformylation and much of the hydrogenation steps occurs in the same reactor, thus producing predominately alcohols if the $H_2$ to CO ratio in the feed synthesis is about 2 to 1. This single step process, along with a strong preference of the catalysts for the reaction at the terminal position of linear olefins makes it possible to prepare alcohols with a high linear to branched ratio from mixtures of internal and terminal linear olefins.

The formation of linear aldehydes is also favored by ligand modified rhodium carbonyl catalysts. Typical complex catalyst concentrations contain from 50 ppm to 150 ppm of rhodium. Additional information on commercial oxo-processes is described in Kirk-Othmer, Encyclopedia of Chemical Technology, 3rd edition, Vol. 16, John Wiley & Sons, pp. 637–653.

The $C_4^+$ OTO according to this invention is produced in an oxygenate to olefin process. The oxygenate to olefin process uses small pore, zeolite or non-zeolite molecular sieve catalyst to catalyze conversion of an oxygenate, such as methanol, to primarily $C_2$ to $C_4^+$ olefin. Zeolite molecular sieve are complex crystalline aluminosilicates which form a network of $AlO_2^-$ and $SiO_2$ tetrahedra linked by shared oxygen atoms. The negativity of the tetrahedra is balanced by the inclusion of cations such as alkali or alkaline earth metal ions. In the manufacture of some zeolites, non-metallic cations, such as tetramethylammonium (TMA) or tetrapropylammonium (TPA), are present during synthesis.

Zeolites include materials containing silica and optionally alumina, and materials in which the silica and alumina portions have been replaced in whole or in part with other oxides. For example, germanium oxide, tin oxide, and mixtures thereof can replace the silica portion. Boron oxide, iron oxide, gallium oxide, indium oxide, and mixtures thereof can replace the alumina portion. Unless otherwise specified, the terms "zeolite" and "zeolite material" as used herein, shall mean not only materials containing silicon atoms and, optionally, aluminum atoms in the crystalline lattice structure thereof, but also materials which contain suitable replacement atoms for such silicon and aluminum atoms.

Non-zeolite, silicoaluminophosphate molecular sieves are preferred for use in connection with this invention. These sieves generally comprise a three-dimensional microporous crystal framework structure of $[SiO_2]$, $[AlO_2]$ and $[PO_2]$ tetrahedral units. In general, silicoaluminophosphate molecular sieves comprise a molecular framework of corner-sharing $[SiO_2]$, $[AlO_2]$, and $[PO_2]$ tetrahedral units. This type of framework is effective in converting various oxygenates into olefin products.

It is preferred that the silicoaluminophosphate molecular sieve used in this invention have a relatively low $Si/Al_2$ ratio. In general, the lower the $Si/Al_2$ ratio, the lower the $C_1$–$C_4$ saturates selectivity, particularly propane selectivity. A $Si/Al_2$ ratio of less than 0.65 is desirable, with a $Si/Al_2$ ratio of not greater than 0.40 being preferred, and a $Si/Al_2$ ratio of not greater than 0.32 being particularly preferred. A $Si/Al_2$ ratio of not greater than 0.20 is most preferred.

Silicoaluminophosphate molecular sieves are generally classified as being microporous materials having 8, 10, or 12 membered ring structures. These ring structures can have an average pore size ranging from about 3.5–15 angstroms. Preferred are the small pore SAPO molecular sieves having an average pore size of less than about 5 angstroms, preferably an average pore size ranging from about 3.5 to 5 angstroms, more preferably from 3.5 to 4.2 angstroms. These pore sizes are typical of molecular sieves having 8 membered rings.

Substituted SAPOs can also be used in this invention. These compounds are generally known as MeAPSOs or metal-containing silicoaluminophosphates. The metal can be alkali metals (Group IA), alkaline earth metals (Group IIA), rare earth metals (Group IIIB, including the lanthanide elements), and the transition metals of Groups IB, IIB, IVB, VB, VIIB, VIIB, and VIIIB. Incorporation of the metal component is typically accomplished adding the metal component during synthesis of the molecular sieve. However, post-synthesis ion exchange can also be used as disclosed in U.S. Pat. No. 5,962,762 to Sun et al. and U.S. patent application Ser. No. 09/615,526, the disclosures of which are incorporated herein by reference.

Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. Preferred are SAPO-17, SAPO-18, SAPO-34, SAPO-35, SAPO-44, and SAPO-47, particularly SAPO-17, SAPO-18 and SAPO-34, including the metal containing forms thereof, and mixtures thereof. As used herein, the term mixture is synonymous with combination and is considered a composition of matter having two or more components in varying proportions, regardless of their physical state.

The silicoaluminophosphate molecular sieves are synthesized by hydrothermal crystallization methods generally known in the art. See, for example, U.S. Pat. Nos. 4,440,871; 4,861,743; 5,096,684; and 5,126,308, the methods of making of which are fully incorporated herein by reference. A reaction mixture is formed by mixing together reactive silicon, aluminum and phosphorus components, along with at least one template. Generally the mixture is sealed and heated, preferably under autogenous pressure, to a temperature of at least 100° C., preferably from 100–250° C., until a crystalline product is formed. Formation of the crystalline product can take anywhere from around 2 hours to as much as 2 weeks. In some cases, stirring or seeding with crystalline material will facilitate the formation of the product.

The SAPO molecular sieve structure can be effectively controlled using combinations of templates. For example, in a particularly preferred embodiment, the SAPO molecular sieve is manufactured using a template combination of TEAOH and dipropylamine. This combination results in a particularly desirable SAPO structure for the conversion of oxygenates, particularly methanol and dimethyl ether, to light olefins such as ethylene and propylene.

The silicoaluminophosphate molecular sieve is typically admixed (i.e., blended) with other materials. When blended, the resulting composition is typically referred to as a SAPO catalyst, with the catalyst comprising the SAPO molecular sieve.

Materials which can be blended with the molecular sieve can be various inert or catalytically active materials, or various binder materials. These materials include compositions such as kaolin and other clays, various forms of rare earth metals, metal oxides, other non-zeolite catalyst components, zeolite catalyst components, alumina or alumina sol, titania, zirconia, magnesia, thoria, beryllia, quartz, silica or silica or silica sol, and mixtures thereof. These components are also effective in reducing, inter alia, overall catalyst cost, acting as a thermal sink to assist in heat shielding the catalyst during regeneration, densifying the catalyst and increasing catalyst strength. It is particularly desirable that the inert materials that are used in the catalyst to act as a thermal sink have a heat capacity of from about 0.05 cal/g-° C. to about 1 cal/g-° C., more preferably from about 0.1 to about 0.8 cal/g-° C., most preferably from about 0.1 cal/g-° C. to about 0.5 cal/g-° C.

The catalyst composition preferably comprises about 1% to about 99%, more preferably about 5% to about 90%, and most preferably about 10% to about 80%, by weight of molecular sieve. It is also preferred that the catalyst composition have a particle size of from about $20\mu$ to $3,000\mu$, more preferably about $30\mu$ to $200\mu$, most preferably about $50\mu$ to $150\mu$.

Any standard reactor system can be used in the oxygenate to olefin process including fixed bed, fluid bed or moving bed systems. Preferred reactors are co-current riser reactors and short contact time, countercurrent free-fall reactors. Desirably, the reactor is one in which an oxygenate feedstock can be contacted with a molecular sieve catalyst at a weight hourly space velocity (WHSV) of at least about 1 $hr^{-1}$, preferably in the range of from about 1 $hr^{-1}$ to about 1000 $hr^{-1}$, more preferably in the range of from about 20 $hr^{-1}$ to about 1000 $hr^{-1}$, and most preferably in the range of from about 20 $hr^{-1}$ to about 500 $hr^{-1}$. WHSV is defined herein as the weight of oxygenate, and hydrocarbon which may optionally be in the feed, per hour per weight of the molecular sieve content of the catalyst. Because the catalyst or the feedstock may contain other materials which act as inerts or diluents, the WHSV is calculated on the weight basis of the oxygenate feed, and any hydrocarbon which may be present, and the molecular sieve contained in the catalyst.

Preferably, the oxygenate feed is contacted with the catalyst when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions.

The process can generally be carried out at a wide range of temperatures. An effective operating temperature range can be from about 200° C. to about 700° C., preferably from about 300° C. to about 600° C., more preferably from about 350° C. to about 550° C. At the lower end of the temperature range, the formation of the desired olefin products may become markedly slow. At the upper end of the temperature range, the process may not form an optimum amount of product.

The pressure also may vary over a wide range, including autogenous pressures. Effective pressures may be in, but are not necessarily limited to, oxygenate partial pressures at least 1 psia, preferably at least 5 psia. The process is particularly effective at higher oxygenate partial pressures, such as an oxygenate partial pressure of greater than 20 psia. Preferably, the oxygenate partial pressure is at least about 25 psia, more preferably at least about 30 psia. For practical design purposes it is desirable to operate at a methanol partial pressure of not greater than about 500 psia, preferably not greater than about 400 psia, most preferably not greater than about 300 psia.

The conversion of oxygenates to produce light olefins may be carried out in a variety of catalytic reactors. Reactor types include conventional reactors such as fixed bed reactors, fluid bed reactors, and riser reactors. Preferred reactors are riser reactors.

Having now fully described this invention, it will be appreciated by those skilled in the art that the invention can be performed within a wide range of parameters within what is claimed, without departing from the spirit and scope of the invention.

What is claimed is:

1. A method of making olefin derivatives from an oxygenate comprising:

contacting the oxygenate with a molecular sieve catalyst to produce a hydrocarbon product containing olefin;

separating a C4+ fraction containing four or more carbons from the hydrocarbon product wherein the C4+ fraction comprises from about 80% to about 97% by weight butenes and from about 3% to about 20% by weight butanes;

contacting the C4+ fraction with an oligomerization catalyst to produce a product containing higher olefin and a vent stream;

separating the vent stream from the higher olefin; and contacting a portion of the separated vent stream with the oligomerzation catalyst.

2. The method of claim 1 wherein the butenes comprise from about 20% to about 40% by weight 1-butene, and from about 60% to about 80% by weight 2-butene.

3. The method of claim 1 wherein the olefin product comprises less than 20 ppmw by weight of an individual contaminant, the individual contaminents selected from the group consisting of hydrogen sulfide, carbonyl sulfide, and arsine.

4. The method of claim 1 wherein the molecular sieve catalyst is selected from the group consisting of SAPO-17, SAPO-18, SAPO-34, SAPO-35, SAPO-44, SAPO-56, ZSM-5, ZSM-22, ZSM-35, the metal containing forms of each thereof, and mixtures thereof.

5. The method of claim 1 wherein the oligomerization catalyst is selected from the group consisting of nickel-alkyl aluminum, solid phosphoric acid, nickel-oxide, and ZSM-57.

6. The method of claim 1 further comprising contacting a portion of the product containing higher olefin with a hydroformylation catalyst.

7. The method of claim 1 further comprising separating octenes from the product containing higher olefin and contacting a portion of the octenes with a hydroformylation catalyst to form nonanyl alcohols.

8. The method of claim 1 further comprising separating nonenes from the product containing higher olefin and contacting a portion of the nonenes with a hydroformylation catalyst to form decyl alcohols.

9. The method of claim 1 further comprising separating dodecenes from the product containing higher olefin and contacting a portion of the dodecenes with a hydrogenation catalyst to form dodecanes.

* * * * *